US007346648B1

(12) United States Patent
Seliger

(10) Patent No.: US 7,346,648 B1
(45) Date of Patent: *Mar. 18, 2008

(54) CONTEXT MANAGEMENT SERVER APPLIANCE

(75) Inventor: Robert Seliger, Winchester, MA (US)

(73) Assignee: Sentillion, Inc., Andover, MA (US)

( * ) Notice: Subject to any disclaimer, the term of this patent is extended or adjusted under 35 U.S.C. 154(b) by 725 days.

This patent is subject to a terminal disclaimer.

(21) Appl. No.: 09/583,301

(22) Filed: May 30, 2000

Related U.S. Application Data

(63) Continuation-in-part of application No. 09/545,396, filed on Apr. 7, 2000, now Pat. No. 6,993,556.

(60) Provisional application No. 60/139,235, filed on Jun. 14, 1999, provisional application No. 60/136,670, filed on May 28, 1999.

(51) Int. Cl.
*G06F 15/16* (2006.01)

(52) U.S. Cl. .................... 709/203; 709/217; 709/219; 709/229; 718/107; 718/108; 705/2; 705/3; 705/4

(58) Field of Classification Search ........ 709/202–203, 709/217, 219, 229; 718/107–108; 705/2–4
See application file for complete search history.

(56) References Cited

U.S. PATENT DOCUMENTS 5,546,580 A * 8/1996 Seliger et al. ................. 707/8
5,664,109 A * 9/1997 Johnson et al. ................ 705/2
5,862,377 A * 1/1999 Lee ........................... 719/329
5,964,836 A * 10/1999 Rowe et al. ................ 709/221
6,064,973 A * 5/2000 Smith et al. ................... 705/7
6,119,145 A * 9/2000 Ikeda et al. ................ 709/203
6,134,594 A * 10/2000 Helland et al. ............. 709/229
6,138,120 A * 10/2000 Gongwer et al. ............. 707/10
6,205,476 B1 * 3/2001 Hayes, Jr. ................... 709/220
6,237,092 B1 * 5/2001 Hayes, Jr. ................... 713/100
6,260,021 B1 * 7/2001 Wong et al. ................... 705/2
6,345,294 B1 * 2/2002 O'Toole et al. ............. 709/222
6,377,994 B1 * 4/2002 Ault et al. .................. 709/229
6,401,138 B1 * 6/2002 Judge et al. ................ 719/328
6,567,852 B2 * 5/2003 Besaw et al. ............... 709/228

FOREIGN PATENT DOCUMENTS

| EP | 0 459 912 A2 | 12/1991 |
| EP | 0 540 151 A2 | 5/1993 |
| EP | 0 803 808 A2 | 10/1997 |
| GB | 2 305 087 A | 3/1997 |

(Continued)

OTHER PUBLICATIONS

Context Management ("CCOW") Specification Subject Data Definitions, Version CM-1.1, Nov. 6, 1999, pp. 1-28.
Context Management ("CCOW") Specification User Interface: Microsoft Windows, Version CM-1.1, Nov. 6, 1999, pp. 1-18.

(Continued)

*Primary Examiner*—LaShonda Jacobs
(74) *Attorney, Agent, or Firm*—Richard R. Giunta; Wolf Greenfield & Sacks, P.C.

(57) ABSTRACT

Server appliances provide context management functionality in the healthcare field and other fields. The server appliances may present themselves on a network as one or more World Wide Web sites accessible to applications whose context is managed.

25 Claims, 3 Drawing Sheets

FOREIGN PATENT DOCUMENTS

| | | |
|---|---|---|
| GB | 2 305 747 A | 4/1997 |
| GB | 2 323 458 A | 9/1998 |
| WO | WO91/12583 A1 | 8/1991 |
| WO | WO95/03580 A1 | 2/1995 |

OTHER PUBLICATIONS

Context Management CCOW Specification Component Technology Mapping: Active X, Version CM-1.1, Nov. 6, 1999, pp. 1-48.

Context Management (CCOW) Specification Technology- and Subject -Independent Component, Architecture Version CM-1.1, Nov. 6, 1999, pp. 1-228.

Clinical Context Working Group: "The Clinical Context Object Workgroup: Its Standard and Methods" Internet Document: Clinical Context Object Working Group White Paper, Online; Feb. 16, 1998, XP002154044, <URL:http://www.h17.org/library/committees/sigvi/CCOW_white_paper.doc> retrieved on Nov. 11, 2000.

V. Jagannathan et al.; Objects in Healthcare—Focus on Standards, Standard View, ACM, Mar. 1, 1998, pp. 22-26, XP002154046.

Hewlett-Packard Company, "A method for CCOW patient link enabling web-based applications," Feb. 17, 1998, pp. 1-10.

* cited by examiner

CONTEXT MANAGEMENT SERVER APPLIANCE

CROSS-REFERENCE TO RELATED APPLICATIONS

The present application claims domestic priority under 35 U.S.C. §119(e) to U.S. Patent Application Ser. No. 60/136,670, filed May 28, 1999, and to U.S. Patent Application Ser. No. 60/139,235, filed Jun. 14, 1999, both of which are incorporated herein by reference. This application is a continuation-in-part of U.S. patent application Ser. No. 09/545,396, filed Apr. 7, 2000, now U.S. Pat. No. 6,993,556, which is incorporated herein by reference.

BACKGROUND OF THE INVENTION

1. Field of the Invention

The present invention relates to context management systems. More particularly, the invention relates to systems in which context management software is configured as a server. Yet more particularly, the invention relates to a server appliance including a standalone computer and software system, which performs context management over a network. In some aspects, the invention relates to such a server appliance, which is applicable to context management of healthcare applications.

2. Related Art

There are many businesses or fields of endeavor, which rely on the use of plural desktop computer applications. One such field is the modern practice of medicine. In such a setting, users quite often find themselves entering and reentering similar information over and over. For example, a single user may have to repeat login information in plural applications, followed by the same or similar client information. Such information that defines the environment in which each application operates is known as context. That is, context is a collection of data items and corresponding values, wherein the items represent information required in common between plural applications in an industry or business setting. For example, in health care, a patient identifier (patient ID) is an item which is part of the context in which plural clinical applications may participate, or share.

In the modern practice of medicine, a physician or other professional or staff member may need to store, retrieve, analyze, etc. various types of patient data. The patient data to be processed may be clinical; e.g. x-ray images or blood work results, or may be financial, e.g. insurance cover and billing history. Thus, clinical applications, such as those to store, retrieve and display x-ray images and those to store, retrieve and display blood work results have inputs and outputs which fall into two broad classes: highly specialized, work product specific I/O; and more general, context-related I/O.

The desirability of managing context information, so that a user at a workstation need not reenter information such as user identification (user ID) or patient identification (patient ID) has long been recognized.

A standard known as Health Level Seven Context Management Specification Version CM-1.1 was promulgated by the Health Level Seven (HL7) Clinical Context Object Workgroup (CCOW) on Nov. 6, 1999, incorporated herein in its entirety by reference, to define an interface and other architectural definitions of a Context Management Architecture (CMA), whereby clinical applications interact with a Context Manager to manage context information across a range of clinical and other health care related applications.

At this time, there is no other known, comprehensive context management software packages available. Some small steps have been taken for example to share context amongst one publisher's own titles, using proprietary methods absent a context manager, or to permit a user to sign onto a single application which transfers user context to plural other applications. However, no context manager handling both user and patient context is known, much less a complete system with central administration of the context management process.

A context management administrator is described in detail in U.S. patent application Ser. No. 09/545,396, referred to above.

Context managers and context management administration software require communication from a user via a user interface. Conventional context managers and context management administrators therefore require a console or monitor and keyboard connected to the computer system on which they execute, in order for the user to communicate therewith. A context management administrator may communicate directly with one or more context managers residing on the same computer system. Alternatively, they may communicate through a network.

Likewise a context manager may execute on a computer system in common with the applications whose context is managed, or may execute on a remote computer system, communicating with the applications over a network.

A server appliance is a relatively new type of computing device. The server appliance is a network-connected server that provides a service to multiple client computers. A client requests the server to perform a specific task, such as returning a response to a database query. The server performs the task and returns the result of having performed the task back to the client.

However, unlike traditional computing servers that provide general-purpose platforms for a wide range of computing tasks, a server appliance is singular in purpose.

A server appliance contains specialized software, and possibly specialized hardware, as well, to enable it to achieve its specialized purpose. Server appliances can therefore be optimized for the specific tasks that they may be designed to perform, thereby reducing the server cost and complexity as compared to the cost and complexity of general-purpose servers.

Conventional commercially available server appliances include print server appliances, whose only function is to queue print jobs and route them to appropriate printers; web server appliances, whose only function is to host a single web site or small group of web sites; electronic mail server appliances, whose only function is to host electronic mail services; and, file server appliances, whose only function is to centrally store and retrieve computer files.

The computing hardware on which server appliances are built conventionally includes a central processing unit, memory and long term data storage, all packaged within a single unit. The unit conventionally has only a power supply input and a network input/output (I/O) port. The network I/O port may connect the server appliance to a computer network using any conventional networking hardware, including but not limited to a modem connection, an Ethernet connection, a universal serial bus (USB) connection, etc.

The user controls on a server appliance are conventionally very simple. There may be no controls at all, only a power connection and a network connection, as noted above. Alternatively, there may simply be an on/off switch.

SUMMARY OF THE INVENTION

The present invention overcomes problems with the conventional approaches to hosting context management and context management administration software by providing, according to various aspects and embodiments thereof, a turnkey system providing context management through a network. Embodiments of the invention can bootstrap themselves into operation after only being connected to a power supply and network.

One embodiment of the invention in a context management server appliance includes a computer system and memory executing a stored set of instruction. The computer system has a power supply input and a network input/output (I/O) port. The memory includes a memory in which is stored a set of instructions defining a context management server which delivers context management information to client applications and a memory in which is stored a set of instructions defining a software interface for administering the context management server over the network using a general-purpose client interface. According to another embodiment of the invention, the context management server appliance further includes a memory in which is stored configuration information for the context management server, whereby the context management server can bootstrap without requiring user intervention. When such an embodiment can bootstrap independently of user intervention, there may also be a memory in which is stored a set of instructions which when executed connect the server appliance to the network absent user intervention. According to another embodiment of the context management server appliance there may be included a memory in which is stored a set of instructions which when executed balance a processing load on the server appliance with a processing load on another server appliance. According to yet another embodiment of the invention, the context management server appliance includes a memory in which is stored a set of instructions which when executed transfers a processing load from a failed server appliance to another server appliance.

Some embodiments of the invention may use servers, which communicate using a standard protocol such as the Hypertext Transport Protocol used in the World Wide Web of the global computer network, the Internet. In such an embodiment, applications can access the context management server through a World Wide Web universal resource locator (URL) on the global Internet. Such a URL need not provide access by a user of a conventional browser client to any information, but may be accessible only to application programs whose context are managed. The protection may use user ID and password, encryption and other trusted transaction systems known in the art.

BRIEF DESCRIPTION OF THE DRAWINGS

In the drawings, in which like reference designations indicate like elements.

DETAILED DESCRIPTION

The invention will be better understood upon reading the following detailed description of some embodiments and aspects thereof in connection with the figures.

In accordance with some embodiments of the invention, a software agent acting on behalf of the user, referred to as a Context Manager (CM), enables applications to establish and maintain a common context on behalf of a user. The context may be organized in a variety of ways. For example, in the healthcare industry, the Health Level Seven Context Management Standard represents clinical context as a set of context subjects. Each subject represents a real-world entity, such as a patient or clinical provider, or a real-world concept, such as a clinical encounter, order, or disease state. Context management is explained in some detail in U.S. patent application Ser. No. 09/545,396, noted above.

When a user performs a relevant application gesture, such as selecting a patient from a list of patients, the application informs the context manager of this fact. The context manager is then responsible for conveying to the other applications that a patient has been selected. Information that identifies the patient is conveyed via the context manager. All of the applications in use then tune their data displays to the selected patient.

Figure 1:
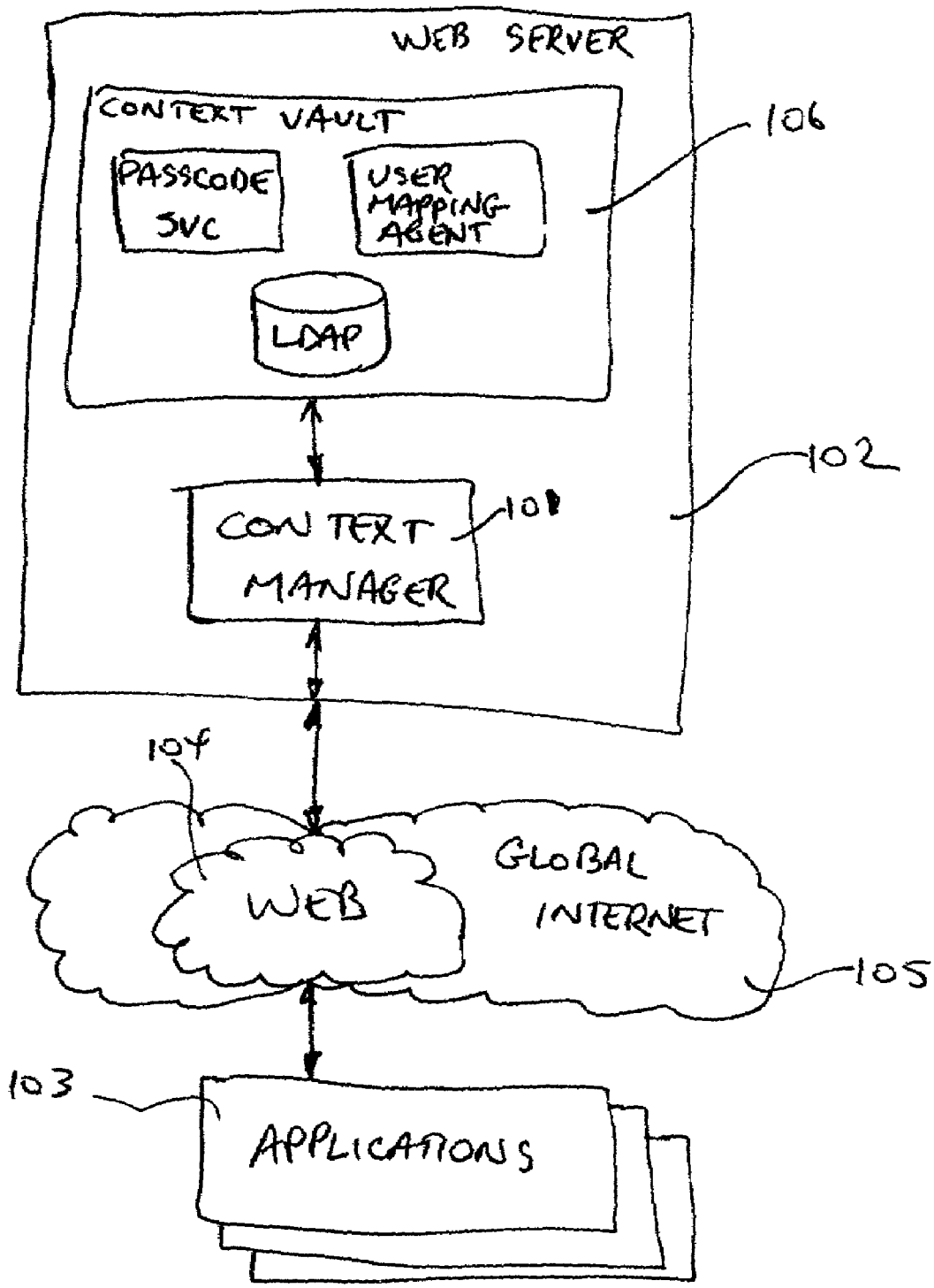
FIG. 1 is a block diagram of a system of context management applications and the context manager operating through a network.

In accordance with one aspect of the invention, shown in FIG. 1, the CM resides and executes on a computer, for example web server 102, separate from the application 103 managed. The applications send information to and receive information from the CM through the World Wide Web 104 over the global Internet 105. Communication is effected using conventional protocols such as TCP/IP and HTTP, as needed.

The Web server 102 shown may be distributed over one or more computers providing the functions of the CM 101 and a context vault 106 providing passcode services and a user-mapping agent (UMA). These functions are all described in detail in U.S. patent application Ser. No. 09/545,396, noted above.

A World Wide Web server provides the only application interface needed for the applications to access the CM and the supporting Context Vaults.

Figure 2:
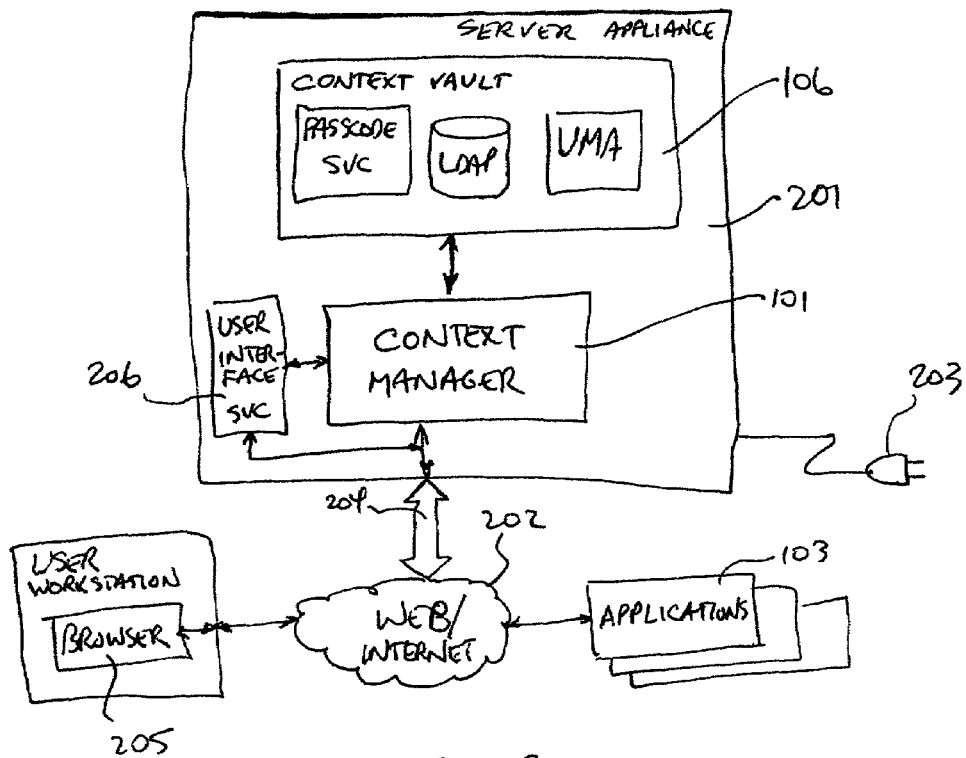
FIG. 2 is a block diagram of one embodiment of a context management server appliance.

In accordance with another aspect of the invention, as shown in FIG. 2, the context manager 101 resides on the server appliance 201, but tracks and maintains a user's context as established by the user upon a particular computer running an application 103. A single context manager 101 may service one, or several, computers and applications. However, each computer perceives that it is interacting with a single context manager 101.

A network connection 202 between each user's computer and the server appliance enables the necessary communication. The network which the server appliance of FIG. 2 is connected to may be the global Internet, for example, or another wide area or local area network. In addition to the context manager 101, the server appliance 201 may contain additional service modules that support the context manager in performing its tasks. As shown in FIG. 2, the appliance may provide the CM 101 and Context Vault 106 functions.

The physical controls for a server appliance are generally limited in nature, and in the simplest case may consist only of an on-off switch. A power connection 203 and a network connection 204 complete this simplest of physical configurations. Devoid of a keyboard, mouse, and other traditional user-interface devices, any interaction with the appliance for the purposes of installation, configuration or maintenance is effected via remote applications that communicate with the appliance through its network connection, for example using conventional browser 205 client software. In such a configuration, the browser 205 would be directed to a particular location 206 in the Web site supported by the appliance, at which a configuration program can be accessed and controlled through an interface displayed by the browser 205 in response to messages from the configuration program 206.

The context management server appliance can be implemented in a variety of ways. One way is to adapt an existing server appliance device by creating and installing the necessary context management software and complementary support tools. The network connection to the Internet would be based upon the TCP/IP protocol upon which a higher-level communication protocol such as HTTP might be used, as mentioned above.

The specific network messages that pertain to context management can be represented in a variety of ways. One example is to define messages using the syntax of HTTP, such that each message represents a specific action for the server to process. For example, an application might send a specific message when it wants to change the data for the current context. It would send a different message if it wanted to obtain the data for the current context.

Figure 3:
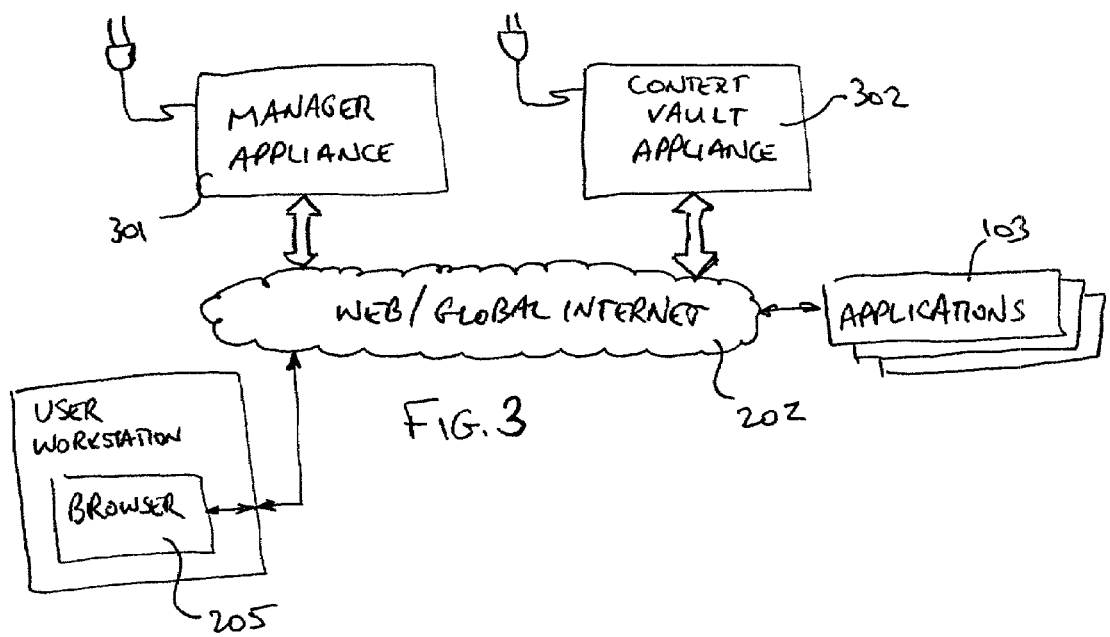
FIG. 3 is a block diagram of another embodiment of the invention constructed using two server appliances.

The functionality of context management can be partitioned, according to another aspect of the invention shown in FIG. 3. In this exemplary partitioning, the CM and Context Vault are each configured to execute on their own server appliance 301 and 302, respectively. The server appliances 301, 302 then communicate with each other through the network 202 to which they are connected. Applications 103 whose context is managed communicate with the CM using TCP/IP and HTTP, for example, as before.

Figure 4:
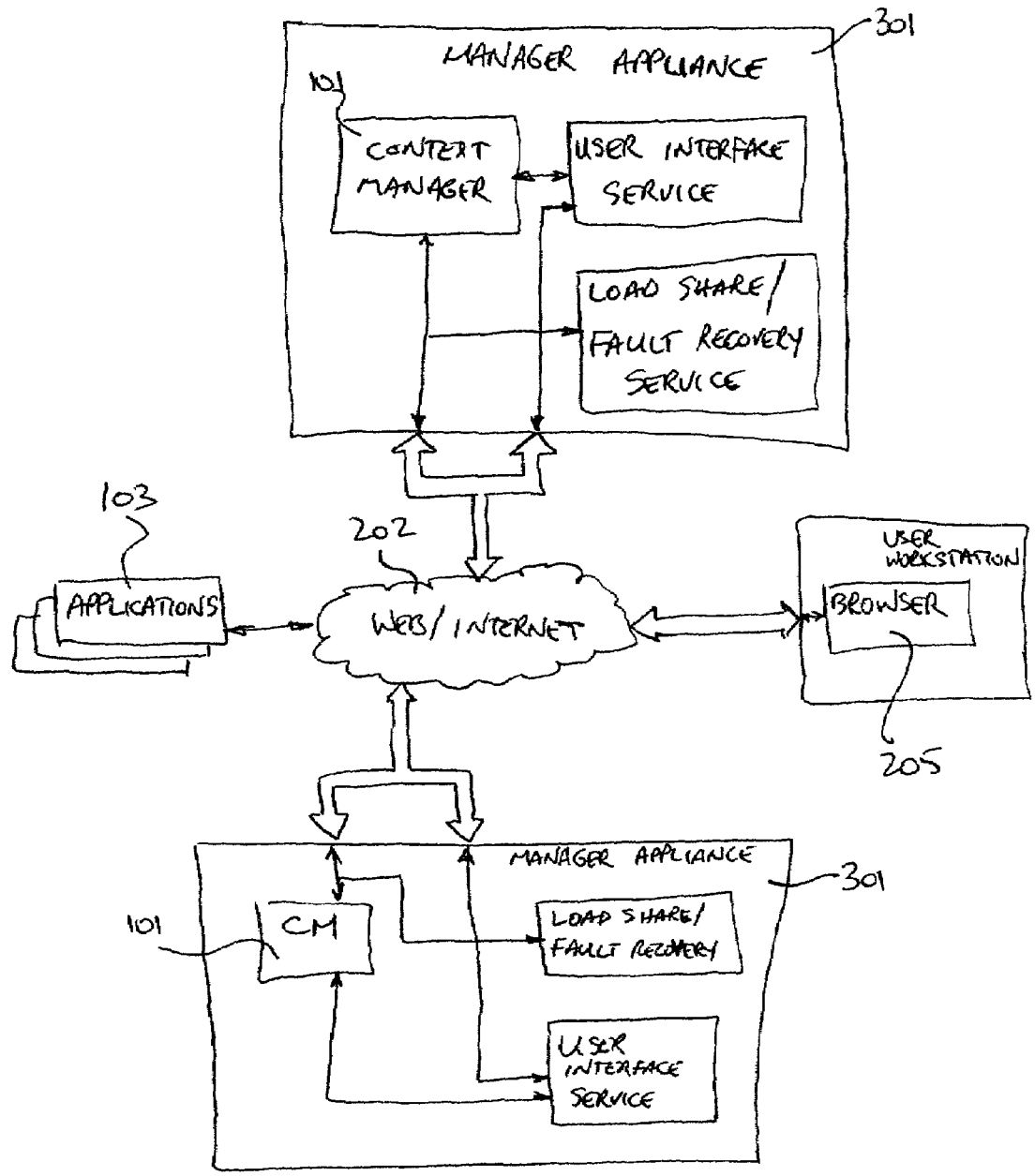
FIG. 4 is a block diagram of yet another embodiment of the invention with built in load sharing and fault tolerant features.

As shown in FIG. 4, plural manager appliances can be connected to the network. When an application addresses a context manager, the communication may be mediated by a service which ensures that the work load of the plurality of context managers is fairly distributed. The load sharing service itself may be distributed amongst the various context managers which communicate with each other and with the managed applications through the network. When a context manager fails or is taken off line for service, the same or a similar service can ensure that context management tasks are suitably redistributed amongst the remaining context management server appliances.

Server appliances embodying aspects of the invention do not merely serve back to the managed applications stored data or simply process input messages. These server appliances perform all of the complex CM functions described in U.S. patent application Ser. No. 09/545,396, as well as serving the result of that activity to the managed applications.

This invention has been motivated by the application of context management to healthcare. However, context management, and therefore a context management server appliance, can be applied to many industries, and as such this invention is not limited to healthcare.

A network connection between each user's computer and the server appliance, and/or between other general-purpose servers and the server appliance, enables the necessary communication. In addition, the server appliance may contain additional modules that enable the server to be remotely configured and supported.

In the healthcare field, the use of a server appliance for hosting the services relating to maintaining a Master Patient Index, and for hosting services relating to Coding data, is particularly unique.

In general, a Master Patient Index (MPI) implements an application service wherein the myriad of identifiers typically assigned by a healthcare organization to represent each person known to the organization are reconciled. This reconciliation enables the unambiguous correlation of information about a person who is represented by different identifiers in different electronic and paper systems. An MPI typically maintains additional descriptive information about each person. This information, usually referred to as demographics data, includes the person's full name, address, telephone number, etc.

There are currently many MPI software products, each implementing various algorithms for correlating person identifiers. However, these products are all deployed on general-purpose servers. In embodiments of this invention, the MPI is deployed within a server appliance, thereby providing an optimized, cost-effective, easier-to-maintain, information utility for the healthcare enterprise.

Another type of healthcare server appliance is a Coding server appliance. In general, coding involves the representation of data or concepts as a numeric value, even if the data or concept is not numeric in nature. The numeric representation enables the data or concept to be annotated in terms of its semantic meaning. This enables the electronic interpretation of meaning and facilitates electronically computed deductions, rules, constraints, and comparisons.

For example, the healthcare industry has defined a variety of schemes for representing medications using coded values. This enables physicians to precisely indicate (either manually or electronically) the particular medication issued, independent of the medication's trade name. Once the coded value is entered, systems can check whether the medication has been appropriately administered, determine how much to charge to the patient's bill, etc.

There are currently many Coding software products, each implementing various algorithms for annotating data with coded values. However, these products are all deployed on general-purpose servers. In this invention, the Coding is deployed within a server appliance, thereby providing an optimized, cost-effective, easier-to-maintain, information utility for the healthcare enterprise.

Embodiments of a healthcare MPI or Coding server appliance can be implemented in a variety of ways. One way is to adapt an existing server appliance device by creating and installing the necessary software and complementary support tools. The network connection is most likely based upon the TCP/IP protocol upon which a higher-level communication protocol such as HTTP might be used.

The specific network messages that pertain to context management can be represented in a variety of ways. One example is to define messages using the syntax of HTTP, such that each message represents a specific action for the server to process. For example, an application might send a specific message to an MPI server appliance when it wants to determine if two identifiers represent the same person. It would send a different message if it wanted to obtain demographics data for a person.

The invention has been illustrated by the foregoing description of a number of aspects and embodiments thereof. Numerous variations contemplated as within the scope and spirit of the invention should now be apparent to those skilled in the art. The invention should therefore not be limited by the foregoing description, but rather by the properly construed claims, which follow.

What is claimed is:

1. A method for use in a computer system comprising at least a first computer, a second computer and a network that couples the first and second computers, the method comprising an act of:
   (A) sharing a context between at least first and second applications, the first application having a first user interface executing on the first computer, the second application having a second user interface executing on the first computer, the sharing of the context comprising passing context information over the network between the first user interface and a context manager executing on the second computer and between the second user interface and the context manager;
   wherein the first application executes on the first computer and wherein the second application executes remotely from the first computer; and
   wherein the context comprises a data item usable by the first and second applications, the data item having a set of values comprising at least a first value corresponding to the first application and a second value corresponding to the second application, the set of values identifying a subject in the context, and wherein the act of sharing the context comprises, in response to a user of the first computer switching from the first application to the second application, exchanging the value of the data item corresponding to the first application with the value of the data item corresponding to the second application to retain the context.

2. The method of claim 1, wherein the passing of the context information over the network is performed using an Internet-based communication protocol.

3. The method of claim 1, wherein the second computer comprises a Web server.

4. The method of claim 1, wherein the second computer is a publicly accessible server.

5. The method of claim 1, wherein the network comprises the Internet.

6. The method of claim 1, wherein the network comprises a publicly available network.

7. The method of claim 1, wherein the sharing of the context comprises passing the context information using the HTTP protocol.

8. The method of claim 1, wherein the computer system further comprises a third computer and wherein the second application executes on the third computer.

9. The method of claim 8, wherein the third computer is a web server and the second user interface is a browser.

10. The method of claim 1, wherein the computer system further comprises a third computer, wherein the context comprises a first context, and wherein the method comprises an act of:
    (B) sharing a second context between at least third and fourth applications, the third application having a third user interface executing on the third computer, the fourth application having a fourth user interface executing on the first computer, the sharing of the second context comprising passing context information over the network between the third user interface and the context manager executing on the second computer and between the fourth user interface and the context manager.

11. The method of claim 1, wherein the second computer comprises a server appliance.

12. The method of claim 1, wherein the passing of the context information between the first user interface and the context manager comprises passing at least some of the context information from the first user interface to the context manager.

13. The method of claim 1, wherein the passing of the context information between the first user interface and the context manager comprises passing at least some of the context information from the context manager to the first user interface.

14. The method of claim 1, wherein the context information is defined in accordance with a Clinical Context Object Workgroup (CCOW) standard.

15. The method of claim 1, wherein the context information comprises information on at least one of a plurality of subjects comprising a user subject, a patient subject and an encounter subject.

16. The method of claim 1, wherein the act of sharing the context comprises acts of:
    initially establishing the context; and
    maintaining the context.

17. The method of claim 16, wherein the context information comprises information on at least a patient subject; and
    wherein the act of maintaining the context comprises an act of, changing the patient subject from a first value to a second value by passing context information about the changed patient subject over the network between the first user interface and the context manager and between the second user interface and the context manager.

18. The method of claim 16, wherein the context information comprises information on at least an encounter subject; and
    wherein the act of maintaining the context comprises an act of, changing the encounter subject from a first value to a second value by passing context information about the changed encounter subject over the network between the first user interface and the context manager and between the second user interface and the context manager.

19. The method of claim 16, wherein the context information comprises information on at least one subject; and
    wherein the act of maintaining the context comprises an act of, changing the at least one subject from a first value to a second value by passing context information about the changed at least one subject over the network between the first user interface and the context manager and between the second user interface and the context manager.

20. A method for use in a system comprising a first computer, a second computer and a network that couples the first and second computers, the method comprising an act of:
    (A) sharing a context between at least first and second applications having respective first and second user interfaces executing on the first computer, the second application executing on the second computer, the sharing of the context comprising passing context information between the first user interface and the context manager and between the second application and the context manager;
    wherein the first application executes on the first computer; and
    wherein the context comprises a data item usable by the first and second applications, the data item having a set of values comprising at least a first value corresponding to the first application and a second value corresponding to the second application, the set of values identifying a subject in the context, and wherein the act of sharing the context comprises, in response to a user of the first computer switching from the first application to the second application, exchanging the value of the data item corresponding to the first application with the value of the data item corresponding to the second application to retain the context.

21. The method of claim 20, wherein the passing of the context information between the second application and the context manager comprises passing at least some of the context information between the context manager and the second user interface.

22. The method of claim 16, wherein the context information comprises information on at least a user subject; and
wherein the act of maintaining the context comprises an act of, changing the user subject from a first value to a second value by passing context information about the changed user subject over the network between the first user interface and the context manager and between the second user interface and the context manager.

23. The method of claim 20, wherein the act of sharing the context comprises acts of:
initially establishing the context; and
maintaining the context.

24. The method of claim 23, wherein the context information comprises information on at least one subject; and
wherein the act of maintaining the context comprises an act of, changing the at least one subject from a first value to a second value by passing context information about the changed at least one subject between the first user interface and the context manager and between the second application and the context manager.

25. A method for use in a computer system comprising at least a first computer, a second computer and a network that couples the first and second computers, the method comprising an act of:

(A) sharing a context between at least first and second applications, the first application having a first user interface executing on the first computer, the second application having a second user interface executing on the first computer, the sharing of the context comprising passing context information over the network between the first user interface and a context manager executing on the second computer and between the second user interface and the context manager, the context information comprising information on at least one subject;

wherein the act of sharing the context comprises acts of:
initially establishing the context; and
maintaining the context, wherein the act of maintaining the context comprises an act of changing the at least one subject from a first value to a second value by passing context information about the changed at least one subject over the network between the first user interface and the context manager and between the second user interface and the context manager;

wherein the context comprises a data item usable by the first and second applications, the data item having a set of values comprising at least a first value corresponding to the first application and a second value corresponding to the second application, the set of values identifying the at least one subject in the context, and wherein the act of sharing the context comprises, in response to a user of the first computer switching from the first application to the second application, exchanging the value of the data item corresponding to the first application with the value of the data item corresponding to the second application to retain the context.

* * * * *

UNITED STATES PATENT AND TRADEMARK OFFICE
CERTIFICATE OF CORRECTION

PATENT NO. : 7,346,648 B1 Page 1 of 1
APPLICATION NO. : 09/583301
DATED : March 18, 2008
INVENTOR(S) : Robert Seliger and David Fusari It is certified that error appears in the above-identified patent and that said Letters Patent is hereby corrected as shown below:

Title Page
Item (75) should read:
(75) Inventors: Robert Seliger, Winchester, MA (US);
David Fusari, Groton, MA (US)

Signed and Sealed this

Twenty-second Day of June, 2010

David J. Kappos
*Director of the United States Patent and Trademark Office*